United States Patent
Ernst et al.

(10) Patent No.: US 12,162,842 B2
(45) Date of Patent: Dec. 10, 2024

(54) CONVERSION OF GLYCOLALDEHYDE WITH AN AMINATING AGENT

(71) Applicant: BASF SE, Ludwigshafen am Rhein (DE)

(72) Inventors: Martin Ernst, Ludwigshafen am Rhein (DE); Tatjana Huber, Ludwigshafen am Rhein (DE); Johann-Peter Melder, Ludwigshafen am Rhein (DE); Stephanie Jaegli, Ludwigshafen am Rhein (DE); Thomas Krug, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 534 days.

(21) Appl. No.: 17/617,335

(22) PCT Filed: Jun. 2, 2020

(86) PCT No.: PCT/EP2020/065198
§ 371 (c)(1),
(2) Date: Dec. 8, 2021

(87) PCT Pub. No.: WO2020/249426
PCT Pub. Date: Dec. 17, 2020

(65) Prior Publication Data
US 2022/0259139 A1    Aug. 18, 2022

(30) Foreign Application Priority Data

Jun. 11, 2019 (EP) .................................. 19179444
Jun. 11, 2019 (EP) .................................. 19179445
Jun. 11, 2019 (EP) .................................. 19179449

(51) Int. Cl.
| | | |
|---|---|---|
| C07C 29/154 | (2006.01) | |
| C07C 209/16 | (2006.01) | |
| C07C 209/26 | (2006.01) | |
| C07C 209/62 | (2006.01) | |
| C07C 209/84 | (2006.01) | |
| C07C 213/02 | (2006.01) | |
| C07C 213/04 | (2006.01) | |
| C07C 213/08 | (2006.01) | |
| C07C 213/10 | (2006.01) | |
| C07D 251/04 | (2006.01) | |

(52) U.S. Cl.
CPC .......... *C07D 251/04* (2013.01); *C07C 29/154* (2013.01); *C07C 209/16* (2013.01); *C07C 209/26* (2013.01); *C07C 209/62* (2013.01); *C07C 209/84* (2013.01); *C07C 213/02* (2013.01); *C07C 213/04* (2013.01); *C07C 213/08* (2013.01); *C07C 213/10* (2013.01)

(58) Field of Classification Search
None
See application file for complete search history.

(56) References Cited

U.S. PATENT DOCUMENTS

| | | |
|---|---|---|
| 4,322,568 A | 3/1982 | Weiss |
| 4,503,260 A | 3/1985 | Auvil et al. |
| 4,677,213 A | 6/1987 | Kitagawa et al. |
| 6,147,261 A | 11/2000 | Knifton et al. |
| 6,534,441 B1 | 3/2003 | Bartley et al. |
| 7,750,189 B2 | 7/2010 | Kubanek et al. |
| 2004/0022912 A1 | 2/2004 | Majerski et al. |
| 2007/0249871 A1 | 10/2007 | Almeida Lenero et al. |
| 2008/0081931 A1 | 4/2008 | Puckette et al. |
| 2009/0012333 A1 | 1/2009 | Almeida Lenero et al. |

FOREIGN PATENT DOCUMENTS

| | | |
|---|---|---|
| DE | 4400591 A1 | 7/1995 |
| EP | 1106600 A2 | 6/2001 |
| EP | 1697291 A1 | 9/2006 |
| IN | 107011194 A | 8/2017 |
| JP | 03-246248 A | 11/1991 |
| JP | 03-279342 A | 12/1991 |
| WO | 2011/082967 A1 | 7/2011 |
| WO | 2011/082994 A1 | 7/2011 |

OTHER PUBLICATIONS

C. R. Vitasari., "Extraction Of Bio-Based Glycolaldehyde From Wood-Derived Pyrolysis Oils", Doctoral Thesis, Technische Universiteit Eindhoven, 2012, 149 pages.
European Search Report for EP Patent Application No. 19179444.5, Issued on Nov. 25, 2019, 2 pages.
European Search Report for EP Patent Application No. 19179445.2, Issued on Dec. 6, 2019, 3 pages.
European Search Report for EP Patent Application No. 19179449.4, Issued on Dec. 3, 2019, 3 pages.
International Search Report and Written Opinion received for PCT Patent Application No. PCT/EP2020/065198, mailed on Aug. 18, 2020, 7 pages.
Liang, et al., "Production of Primary Amines by Reductive Amination of Biomass-Derived Aldehydes/Ketones", Angewandte Chemie International Edition, vol. 56, Issue 11, Feb. 3, 2017, pp. 3050-3054.
Liang, et al., "Production of Primary Amines by Reductive Amination of Biomass-Derived Aldehydes/Ketones", Angewandte Chemie, vol. 129, Issue 11, Feb. 3, 2017, pp. 3096-3100.
Mohan, et al., "Pyrolysis of Wood/Biomass for Bio-oil :? A Critical Review", Energy & Fuels, vol. 20, Issue 3, Mar. 10, 2006, pp. 848-889.
Pelckmans, et al., "Catalytic Reductive Aminolysis of Reducing Sugars: Elucidation of Reaction Mechanism", ACS Catalysis, vol. 8, Issue 5, Apr. 6, 2018, pp. 4201-4212.

*Primary Examiner* — Sudhakar Katakam
*Assistant Examiner* — Jennifer C Sawyer
(74) *Attorney, Agent, or Firm* — Faegre Drinker Biddle & Reath LLP

(57) ABSTRACT

A process for the conversion of glycolaldehyde with an aminating agent in the presence of hydrogen and of a catalyst in a glycolaldehyde conversion reactor, wherein one or more organic carboxylic acids are fed into the glycolaldehyde conversion reactor.

15 Claims, No Drawings

CONVERSION OF GLYCOLALDEHYDE WITH AN AMINATING AGENT

CROSS-REFERENCE TO RELATED APPLICATIONS

This application is a national stage application (under 35 U.S.C. § 371) of PCT/EP2020/065198, filed Jun. 2, 2020, which claims benefit of European Application Nos. 19179444.5, 19179445.2, and 19179449.4, all filed Jun. 11, 2019, all four of which are incorporated herein by reference in their entirety.

The present invention relates to the reaction of glycolaldehyde with an aminating agent.

Glycolaldehyde appears to be a useful raw material for the production of ethyleneamines and ethanolamines.

U.S. Pat. No. 6,534,441 describes a process for reductive amination of lower aliphatic alkane derivatives using a nickel/rhenium catalyst. A possible feedstock mentioned in the description is glycolaldehyde.

German patent application DE-A1-4400591 describes a process for preparing amino alcohols by reacting hydroxy carbonyl compounds with hydrogen and an aminating agent at temperatures of 0 to 300° C. and pressures of 1 to 400 bar over a catalyst which comprises 50 to 100% by weight of ruthenium. Glycolaldehyde is disclosed as suitable hydroxy carbonyl compound which can be employed in the process.

The conversion of hydroxy alkanals to diamines in the presence of ammonia and hydrogen in the presence of catalysts which comprise nickel or cobalt is disclosed in U.S. Pat. Nos. 6,147,261, 6,147,261 teaches that hydroxy alkanals are very reactive and tends to oligomerization and polymerization.

Although U.S. Pat. No. 6,147,261, DE-A1-4400591 and U.S. Pat. No. 6,534,441 mention the use of glycolaldehyde as a feedstock in a reaction with an aminating agent, the specific reaction demonstrated by examples has not been described.

CN107011194 discloses a method for conversion of glycolaldehyde with different aminating agents, such as ammonia, methylamine, ethylamine and butylamine in the presence of hydrogen using noble metal catalysts which comprise rare earth metals.

The conversion of glycolaldehyde with aminating agents, such as ammonia, in the presence of hydrogen was disclosed in WO2011/082994. Due to glycolaldehyde's tendency to form oligomers, such as the dimer 2,5-dihydroxy-1,4-dioxane, a six-membered ring compound formed having a high thermodynamic stability, the conversion required the pre-activation of non-noble metal amination catalysts to achieve high conversions.

The effect of catalyst pre-activation was later confirmed by Liang et al. (Angew. Chem. 2017, 129, 3096-3100) who studied the conversion of glycolaldehyde with ammonia in the presence hydrogen and Ru-catalysts.

Pelckmans et. Al (ACS Catal. 2018, 8, 4201-4212) studied the reductive amination of various sugars with dimethylamine in the presence of hydrogen and different metal catalysts. It was proposed that glycolaldehyde is formed as an intermediate during the reductive aminolysis of sugars. The authors therefore studied the reaction behavior of pure glycolaldehyde with dimethylamine and hydrogen over a nickel catalyst as a model reaction. High conversions to TMEDA and DMEOA were obtained in MeOH-solutions.

WO2011/082967 discloses the amination of glycolaldehyde with the aminating agents MEA and DEA in the presence of hydrogen and amination catalysts to yield ethanolamines.

Glycolaldehyde is a reducing sugar having a hydroxyl group and a free aldehyde group. In the state of the art, the aminating agent preferably reacts with the aldehyde group to form the respective mono-, di- and triethanolamines.

Object of the present invention was to increase the conversion of the terminal hydroxy groups of glycolaldehyde and of its primary conversion products, the respective mono-, di- or triethanolamines. An increase in the conversion of the terminal hydroxy groups would lead to an increase in valuable di- and tri-amines as well as polyamines or hydroxyamines.

The object is achieved by a process for the conversion of glycolaldehyde with an aminating agent in the presence of hydrogen and of a catalyst in a glycolaldehyde conversion reactor, wherein one or more organic carboxylic acids are fed into the glycolaldehyde conversion reactor.

In the process according to the invention, glycolaldehyde is used.

Glycolaldehyde is commercially available and can be prepared, for example, by oxidizing ethylene glycol (see, for example, JP 3246248 and JP 3279342).

Glycolaldehyde is preferably synthesized by reaction of formaldehyde with carbon monoxide and hydrogen, as described, for example, in US 2009012333, US 2008081931, US 2007249871, EP 1697291, U.S. Pat. Nos. 4,503,260 and 4,322,568.

More preferably, glycolaldehyde can also be obtained from the cracking of aqueous solutions of organic feedstocks, such as sugars or woods, at high temperatures.

In a more preferred embodiment, a glycolaldehyde solution is obtained by the hydrous thermolysis of sugars, such as the process disclosed in US 2004/0022912, which is hereby incorporated by reference. Such processes preferably yield streams of glycolaldehyde and water.

In a further preferred embodiment, a glycolaldehyde solution is obtained by the pyrolysis of wood, such as the processes disclosed by D. Mohan et al. ("Pyrolysis of Wood/Biomass for Bio-Oil", Energy Fuels 2006, 20, 3, 848-889) or by C. R. Vitasari (Extraction of bio-based glycolaldehyde from wood-derived pyrolysis oils Eindhoven: Technische Universiteit Eindhoven DOI: 10.6100/IR738958).

Preferably, the concentration of glycolaldehyde in such streams is in the range of 5 to 50 percent by weight, most preferably 10 to 40 percent by weight and most preferably 15 to 35 percent by weight.

The streams obtained by such processes may comprise other oxygenates, such as formaldehyde, hydroxyacetone (acetol), dihydroxyacetone, glyoxal, methylglyoxal (pyruvaldehyde), acetic acid, levulinic acid, propionic acid, acrylic acid, methanol, acetone and formic acid.

Glycolaldehyde has a strong tendency to form oligomers in the pure state or in solutions. In particular the dimer 2,5-dihydroxy-1,4-dioxane, a six-membered ring compound having a high thermodynamic stability, is formed in the pure state.

Unless otherwise explicitly stated, all indications of weights and molar ratios of glycolaldehyde in this specification refer to monomeric glycolaldehyde, irrespective of whether the glycolaldehyde used in the conversion is present in the monomeric or oligomeric form.

A further starting material used in the process according to the invention is an aminating agent.

The aminating agents used in the hydrogenating amination of alcohols, aldehydes or ketones in the presence of hydrogen may be either ammonia or primary or secondary aliphatic or cycloaliphatic or aromatic amines.

The aminating agent is preferably a nitrogen compound of the formula I

in which

R$^1$, R$^2$ are each hydrogen (H), alkyl such as C$_{1-20}$-alkyl, cycloalkyl such as C$_{3-12}$-cycloalkyl, alkoxyalkyl such as C$_{2-30}$-alkoxyalkyl, dialkylaminoalkyl such as C$_{3-30}$-dialkylaminoalkyl, aryl, aralkyl such as C$_{7-20}$-aralkyl, and alkylaryl such as C$_{7-20}$-alkylaryl, or together are —(CH$_2$)$_j$—X—(CH$_2$)$_k$—, X is CH$_2$, CHR$^3$, oxygen (O), sulfur (S) or NR$^3$, R$^3$ is hydrogen (H), alkyl such as C$_{1-4}$-alkyl, alkylphenyl such as C$_{7-40}$-alkylphenyl, j, k are each integers from 1 to 4.

Preference is given to aminating agents in which R$^1$ and R$^2$ are each—the same or different—alkyl, such as C$_{1-20}$-alkyl, preferably C$_{1-12}$-alkyl, more preferably C$_{1-8}$-alkyl and most preferably C$_{1-4}$-alkyl.

In a preferred embodiment, the following mono- and dialkylamines are used as aminating agents: monomethylamine, dimethylamine, monoethylamine, diethylamine, n-propylamine, di-n-propylamine, iso-propylamine, di-iso-propylamine, iso-propyl-ethylamine, n-butylamine, di-n-butylamine, s-butylamine, di-s-butylamine, iso-butylamine, di-iso-butylamine, n-pentylamine, di-n-pentylamine, s-pentylamine, di-s-pentylamine, iso-pentylamine, di-iso-pentylamine, n-hexylamine, di-n-hexylamine, s-hexylamine, di-s-hexylamine, iso-hexylamine and di-iso-hexylamin.

Especially preferred aminating agents are monomethylamine, monoethylamine, dimethylamine and diethylamine. Very particular preference is given to using dimethylamine and diethylamine as aminating agents.

A further feedstock used in the process according to the invention is hydrogen

The hydrogen is generally used in technical grade purity. The hydrogen can also be used in the form of a hydrogen-comprising gas, i.e. in mixtures with other inert gases, such as nitrogen, helium, neon, argon or carbon dioxide. Preference is given, however, to using pure hydrogen or essentially pure hydrogen, for example hydrogen with a content of more than 99% by weight of hydrogen, preferably more than 99.9% by weight of hydrogen, more preferably more than 99.99% by weight of hydrogen, especially more than 99.999% by weight of hydrogen.

In a preferred embodiment, the reaction of glycolaldehyde with an aminating agent is carried out in the presence of one or more solvents.

The solvent used may be any solvent which is inert under the reaction conditions and has a sufficient solubility for the reactants and reaction products.

Preferably the one or more solvents are water, ethers, preferably methyl tert-butyl ether, ethyl tert-butyl ether, dioxane, tetrahydrofuran (THF), proglyme, diglyme, polyglymes and generally ethers of oligo- and polypropyleneoxides and oligo- and polyethyleneoxides or mixed oligo- or polyalkyleneoxides and alcohols, preferably methanol, ethanol and iso-propanol.

Useful solvents also include suitable mixtures of the solvents listed above.

Particularly preferred solvents are methanol, glymes, THF and water.

Most preferably mixtures of water and tetrahydrofuran are used as solvents, wherein the molar ratio of water to THF is in the range of 1:1 to 20:1, more preferably 4:1 to 15:1 and most preferably 5:1 to 10:1.

Particularly preferred solvents also include the reaction products of the inventive reaction of glycolaldehyde and the aminating agent.

The conversion of glycolaldehyde with the aminating agent is conducted in the presence of a catalyst.

The catalysts may in principle comprise nickel, cobalt, iron, copper, chromium, manganese, copper, molybdenum, tungsten and/or other metals of groups 8 and/or 9 and/or 10 and/or 11 of the periodic table of the elements Preference is given to using catalysts which comprise at least one metal selected from the group consisting of Cu, Co, Ni, Pd, Pt, Ru, Rh, Ag, Au, Re and Ir.

More preference is given to using catalysts which comprise at least one metal selected from the group consisting of Cu, Co, Ni, Pd, Pt and Ru.

The abovementioned catalysts can be doped in a customary manner with promoters, for example with chromium, iron, cobalt, manganese, molybdenum, titanium, tin, metals of the alkali metal group, metals of the alkaline earth metal group and/or phosphorus.

The catalyst can be a supported or unsupported catalyst.

Suitable support materials are carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

In a preferred embodiment of the invention, catalysts of the Raney type are being used.

As Raney catalysts, Raney cobalt catalysts, Raney nickel catalysts and/or Raney copper catalysts are preferably used. Raney cobalt catalysts are particularly preferred.

In a further preferred embodiment of the invention the catalysts are prepared by reduction of a catalyst precursor, in which the aforementioned metals are present in the form of oxygen comprising compounds, such as their oxides, carbonates or hydrogencarbonates.

The catalyst precursors can be prepared by known processes, for example by precipitation, precipitative application or impregnation.

Impregnation:

In a preferred embodiment, catalyst precursors which are prepared by impregnating support materials are used in the process according to the invention (impregnated catalyst precursors).

The support materials used in the impregnation can, for example, be used in the form of powders or shaped bodies, such as extrudates, tablets, spheres or rings. Support material suitable for fluidized bed reactors is preferably obtained by spray drying.

Useful support materials include, for example, carbon such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The abovementioned support materials can be impregnated by the customary methods (A. B. Stiles, Catalyst Manufacture—Laboratory and Commercial Preparations, Marcel Dekker, New York, 1983), for example by applying a metal salt solution in one or more impregnation stages. Useful metal salts generally include water-soluble metal salts, such as the nitrates, acetates or chlorides of the corresponding catalytically active components or the doping elements, such as cobalt nitrate or cobalt chloride. Thereafter, the impregnated support material is generally dried and optionally calcined.

The impregnation can also be affected by the so-called "incipient wetness method", in which the support material is moistened with the impregnating solution up to a maximum of saturation according to its water absorption capacity. However, the impregnation can also be affected in supernatant solution.

In the case of multistage impregnation processes, it is appropriate to dry and if appropriate to calcine between individual impregnation steps. Multistage impregnation can be employed advantageously when the support material is to be contacted with metal salts in a relatively large amount.

To apply a plurality of metal components to the support material, the impregnation can be affected simultaneously with all metal salts or in any desired sequence of the individual metal salts.

In a further preferred embodiment, catalyst precursors are prepared by means of a coprecipitation of all of their components. To this end, in general, a soluble compound of the corresponding active component and of the doping elements, and optionally a soluble compound of a support material is admixed with a precipitant in a liquid while heating and while stirring until the precipitation is complete The liquid used is generally water.

Useful soluble compounds of the active components typically include the corresponding metal salts, such as the nitrates, sulfates, acetates or chlorides of the aforementioned metals. The soluble compounds of a support material used are generally water-soluble compounds of Ti, Al, Zr, Si etc., for example the water-soluble nitrates, sulfates, acetates or chlorides of these elements.

The soluble compounds of the doping elements used are generally water-soluble compounds of the doping elements, for example the water-soluble nitrates, sulfates, acetates or chlorides of these elements.

Catalyst precursors can also be prepared by precipitative application.

Precipitative application is understood to mean a preparation method in which a sparingly soluble or insoluble support material is suspended in a liquid and then soluble compounds, such as soluble metal salts, of the appropriate metal oxides, are added, which are then precipitated onto the suspended support by adding a precipitant (for example, described in EP-A2-1 106 600, page 4, and A. B. Stiles, Catalyst Manufacture, Marcel Dekker, Inc., 1983, page 15).

Useful sparingly soluble or insoluble support materials include, for example, carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present in the form of powder or spall.

The liquid used, in which the support material is suspended, is typically water.

Useful soluble compounds include the aforementioned soluble compounds of the active components or of the doping elements.

Typically, in the precipitation reactions, the soluble compounds are precipitated as sparingly soluble or insoluble basic salts by adding a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be performed, for example, at temperatures of 20 to 100° C., preferably 30 to 90° C., especially at 50 to 70° C.

The precipitates formed in the precipitation reactions are generally chemically inhomogeneous and generally comprise mixtures of the oxides, oxide hydrates, hydroxides, carbonates and/or hydrogencarbonates of the metals used. It may be found to be favorable for the filterability of the precipitates when they are aged, i.e. when they are left alone for a certain time after the precipitation, if appropriate under hot conditions or while passing air through.

The precipitates obtained by these precipitation processes are typically processed by washing, drying, calcining and conditioning them.

After washing, the precipitates are generally dried at 80 to 200° C., preferably 100 to 150° C., and then calcined.

The calcination is performed generally at temperatures between 300 and 800° C., preferably 350 to 600° C., especially at 450 to 550° C.

After the calcination, the pulverulent catalyst precursors obtained by precipitation reactions are typically conditioned.

The conditioning can be affected, for example, by adjusting the precipitation catalyst to a particular particle size by grinding.

After the grinding, the catalyst precursor obtained by precipitation reactions can be mixed with shaping assistants such as graphite or stearic acid and processed further to shaped bodies.

Common processes for shaping are described, for example, in Ullmann [Ullmann's Encyclopaedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff].

As described in the references cited, the process for shaping can provide shaped bodies in any three-dimensional shape, for example round, angular, elongated or the like, for example in the form of extrudates, tablets, granules, spheres, cylinders or grains. Common processes for shaping are, for example, extrusion, tableting, i.e. mechanical pressing, or pelletizing, i.e. compacting by circular and/or rotating motions.

The conditioning or shaping is generally followed by a heat treatment. The temperatures in the heat treatment typically correspond to the temperatures in the calcination.

The catalyst precursors obtained by precipitation reactions comprise the catalytically active components in the form of a mixture of oxygen compounds thereof, i.e. especially as the oxides, mixed oxides and/or hydroxides. The catalyst precursors thus prepared can be stored as such.

The catalyst which is used in the process according to the invention is obtained by reducing catalyst precursors which have been prepared by impregnation or precipitation as described above after the calcination or conditioning.

The reduction of the dry, generally pulverulent catalyst precursor can be performed at elevated temperature in a moving or stationary reduction oven.

The reducing agent used is typically hydrogen or a hydrogen-comprising gas.

The hydrogen is generally used in technical grade purity. The hydrogen can also be used in the form of a hydrogen-comprising gas, i.e. in admixtures with other inert gases, such as nitrogen, helium, neon, argon or carbon dioxide. The hydrogen stream can also be recycled into the reduction as cycle gas, optionally mixed with fresh hydrogen and optionally after removing water by condensation.

The catalyst precursor is preferably reduced in a reactor in which the shaped catalyst bodies are arranged as a fixed bed. The catalyst precursor is more preferably reduced in the same reactor in which the conversion of glycolaldehyde with the aminating agent is carried out.

Alternatively, the catalyst precursor can be reduced in a separate fluidized bed reactor in the fluidized bed.

The catalyst precursor is generally reduced at reduction temperatures of 50 to 600° C., especially of 100 to 500° C., more preferably of 150 to 450° C.

The partial hydrogen pressure is generally from 1 to 300 bar, especially from 1 to 200 bar, more preferably from 1 to 100 bar, where the pressure figures here and hereinafter are based on the absolute measured pressure.

The duration of the reduction is preferably 1 to 20 hours and more preferably 5 to 15 hours.

During the reduction, a solvent can be supplied in order to remove water of reaction which forms and/or in order, for example, to be able to heat the reactor more rapidly and/or to be able to better remove the heat during the reduction. In this case, the solvent can also be supplied in supercritical form.

Suitable solvents used may be the above-described solvents. Preferred solvents are water; ethers such as methyl tert-butyl ether, ethyl tert-butyl ether, dioxane or tetrahydrofuran. Particular preference is given to water or tetrahydrofuran. Suitable solvents likewise include suitable mixtures.

The catalyst precursor can also be reduced in suspension, for example in a stirred autoclave. The temperatures are generally within a range from 50 to 300° C., especially from 100 to 250° C., more preferably from 120 to 200° C.

The reduction in suspension is generally performed at a partial hydrogen pressure of 1 to 300 bar, preferably from 10 to 250 bar, more preferably from 30 to 200 bar. Useful solvents include the aforementioned solvents.

The duration of the reduction in suspension is preferably 5 to 20 hours, more preferably 8 to 15 hours.

The catalyst can be handled under inert conditions after the reduction. The catalyst can preferably be handled and stored under an inert gas such as nitrogen, or under an inert liquid, for example an alcohol, water or the product of the particular reaction for which the catalyst is used. If appropriate, the catalyst must then be freed of the inert liquid before commencement of the actual reaction.

The storage of the catalyst under inert substances enables uncomplicated and safe handling and storage of the catalyst.

After the reduction, the catalyst can also be contacted with an oxygen-comprising gas stream such as air or a mixture of air with nitrogen. This affords a passivated catalyst. The passivated catalyst generally has a protective oxide layer. This protective oxide layer simplifies the handling and storage of the catalyst, such that, for example, the installation of the passivated catalyst into the reactor is simplified.

After passivation, the catalyst is usually activated. A catalyst can be activated by reducing a passivated catalyst. A passivated catalyst can be reduced as described above by treating the passivated catalyst with hydrogen or a hydrogen-comprising gas. The reduction conditions correspond generally to the reduction conditions employed in the reduction of the catalyst precursors. The activation generally eliminates the protective passivation layer.

An activated catalyst has to be handled under inert conditions during and after the activating reduction thereof.

The activated catalyst is preferably handled and stored under an inert gas, such as nitrogen, or under an inert liquid, for example an alcohol, water or the product of the particular reaction for which the catalyst is used. If appropriate, the activated catalyst then has to be freed of the inert liquid before commencement of the actual reaction.

Activation of the catalyst can also occur in situ during conversion step in which glycolaldehyde is converted with an aminating agent.

When an aqueous solvent is present during the conversion of glycolaldehyde, such as mixtures of water and THF, it is preferred to contact the glycolaldehyde with an activated or reduced catalyst.

When a non-aqueous solvent is present during the conversion of glycolaldehyde, such as THF or methanol, it is preferred to contact the glycolaldehyde with a passivated or unreduced catalyst and to activate or reduce the catalyst in-situ with the hydrogen present during the conversion of the glycolaldehyde with the aminating agent.

The process according to the invention is characterized therein that one or more organic carboxylic acids are fed into a glycolaldehyde conversion reactor (GA-reactor).

The organic carboxylic acid can be any organic carboxylic acid.

Non-limiting examples of such acids are:

saturated aliphatic monocarboxylic acids,
such as formic, acetic, propionic, butyric, ethyl butyric, caproic, enanthic, caprylic, pelargonic, capric, undecanoic, lauric, myristic, palmitic, stearic, arachidic and the like, unsaturated aliphatic monocarboxylic acids,
such as acrylic, methacrylic, crotonic, iso-crotonic, decylnic, palmitolic, oleic, linoleic and the like, saturated aliphatic dicarboxylic acids,
such as oxalic, malonic, succinic, glutaric, adipic, pimelic, suberic, azelaic, sebacic and the like, unsaturated aliphatic dicarboxylic acids,
such as maleic, fumaric, itaconic, citraconic, mesaconic and the like, aryl carboxylic acids,
such as benzoic acid, napthoic acid, phthalic acid, isophthalic acid, terephthalic acid, naphthalic acid, pyromelletic acid, toluic acids, and acid esters of polycarboxylic acids such as alkyl acid phthalates and the like, hydroxy carboxylic acids,
such as hydroxy acetic acid, hydroxy propionic acid, ethylidene lactic acid, hydroxy butyric acid, α-hydroxy isobutryric acid, hydroxy caproic acid, hydroxy stearic acid, tartronic acid, tartaric acid, malic acid, hydroxy benzoic acid and the like.

keto acids,
such a pyruvic acid, oxoloacetic acid, levulinic acid

Preferred acids of the aforementioned groups comprise the monocarboxylic acids containing from 1 to 8 carbon atoms, in particular formic acid, acetic acid, propionic acid, butyric acid, valeric acid, caproic acid, enanthic acid, caprylic acid, pelargonic acid, capric acid, acrylic acid dicarboxylic acids containing from 2 to 8 carbon atoms, in particular oxalic acid, maleic acid, succinic acid, glutaric acid, adipic acid, pimelic acid, suberic acid, azelaic acid, sebacic acid, hydroxy-carboxylic acids from 2 to 8 carbon atoms, in particular glycolic acid, lactic acid, citric acid and mandelic acid More preferably, the one or more organic carboxylic acids are selected from the group consisting of formic acid, acetic acid, propionic acid, acrylic acid, levulic acid, lactic acid, glycolic acid and pyruvic acid.

Most preferably, the one or more organic carboxylic acids are selected from the group consisting of formic acid and acetic acid.

The process according to the invention can be performed continuously, batchwise or semi-continuously in a glycol-conversion reactor (GA-reactor).

Typical GA-reactors are, for example, high-pressure stirred tank reactors, autoclaves, fixed bed reactors, fluidized bed reactors, moving beds, circulating fluidized beds, salt bath reactors, plate heat exchangers as reactors, staged reactors with a plurality of stages with or without heat exchange and removal/supply of substreams between the trays, in possible embodiments as radial flow or axial flow reactors, continuously stirred tanks, bubble reactors, etc., the reactor used in each case being that suitable for the desired reaction conditions (such as temperature, pressure and residence time).

The GA-reactor preferably is a high-pressure stirred tank reactor, fixed bed reactor or fluidized bed reactor.

In a particularly preferred embodiment, the GA-reactor is a fixed bed reactor or a series of fixed bed reactors.

In a further particularly preferred embodiment, the GA-reactor is a high-pressure stirred tank reactor or a series of stirred tank reactors.

The glycolaldehyde, the aminating agent, the organic carboxylic acid optionally one or more of solvents are fed to the GA-reactor.

These components can be fed separately into the GA-reactor and mixed in the GA-reactor.

In a preferred embodiment, at least two of the components can be mixed to obtain mixed feed streams comprising two or more components.

Mixed feed streams may be obtained by mixing of two or more of the components.

Mixing can be carried in a batch or in a continuous process. Batch mixing may be carried out in the GA-reactor or a mixing vessel, such as a mixing tank. Continuous mixing may be carried out may feeding one or more components into a pipe or the GA-reactor.

The mixing may be carried out using conventional equipment, such as static mixers, mixing nozzles, agitators, stirrers, impellers, turbines, pumps and the like.

In a preferred embodiment, the mixed feed stream ("preferred mixed feed stream") comprises:

5 to 80, preferably 20 to 75 and more preferably 35 to 70 percent by weight of glycolaldehyde;
0.1 to 25, preferably 0.5 to 15, more preferably 1 to 10 percent by weight of organic carboxylic acids;
0.1 to 25, preferably 0.5 to 20, more preferably 1 to 15 percent by weight of other organic components;
rest water;
wherein the percentages are based on the total weight of the mixed feed stream.

Preferably the one or more acids in the preferred mixed feed stream are selected from the group consisting of formic acid, acetic acid, propionic acid, acrylic acid, levulic acid, lactic acid, glycolic acid and pyruvic acid.

The preferred mixed feed stream may additionally comprise other organic components, in particular oxygenates, such as formaldehyde, hydroxyacetone (acetol), dihydroxyacetone, glyoxal, methylglyoxal (pyruvaldehyde), methanol and acetone.

The preferred mixed feed stream may be fed directly into the GA-reactor or it may be mixed with other components, such aminating agents or solvents, to obtain a modified preferred mixed feed stream.

In a more preferred embodiment, the preferred mixed stream is obtained from the cracking of aqueous solutions of organic feedstocks at high temperatures.

More preferably, the preferred mixed feed stream is obtained by the hydrous thermolysis of sugars, such as the process disclosed in US 2004/0022912, which is hereby incorporated by reference or by the pyrolysis of wood as described by D. Mohan et al. ("Pyrolysis of Wood/Biomass for Bio-Oil", Energy Fuels 2006, 20, 3, 848-889) or by C. R. Vitasari (Extraction of bio-based glycolaldehyde from wood-derived pyrolysis oils Eindhoven: Technische Universiteit Eindhoven DOI: 10.6100/IR738958), which are also incorporated herein by reference.

All feed streams which are fed to the GA reactor, including but not limited to the one or more feed or mixed feed streams, comprising the glycolaldehyde, the aminating agent, the solvent and the organic carboxylic acid, are considered to form the reaction mixture.

The amount of solvent present in the reaction mixture is usually in the range of 1 to 95% by weight, preferably 2.5 to 70%, more preferably 5 to 40%, based on the total weight of the reaction mixture, where the total weight of the reaction mixture is composed of the sum of the masses of all feed streams to the GA-reactor.

The molar ratio glycolaldehyde to each selected organic carboxylic acid in the reaction mixture is preferably in the range of 1:1 to 200:1, more preferably 10:1 to 150:1 and most preferably 20:1 to 100:1.

The molar ratio of glycolaldehyde to the total amount of organic carboxylic acids in the reaction mixture is preferably in the range of 1:1 to 600:1, more preferably 10:1 to 450:1 and most preferably 20:1 to 300:1.

The ratio of aminating agent to the glycolaldehyde used is typically within a range from 1:100 to 100:1, preferably 1:1 to 50:1 and more preferably 1:1 to 45:1.

The partial pressure of hydrogen is preferably in the range of 2, 5 to 200 bar, more preferably in the range of 5 to 150 bar, even more preferably in the range of 10 to 100 bar and most preferably in the range of 20 to 50 bar.

In the process according to the invention, glycolaldehyde is reacted with an aminating agent in the presence of hydrogen and a catalyst.

The process according to the invention can be performed continuously, batchwise or semi-continuously in an appropriate glycolaldehyde conversion reactor described above.

The feed streams, such as the separate feed streams, mixed feed streams, preferred mixed feed streams or modified preferred mixed feed streams, can be fed into the GA-reactor, making use of appropriate feed equipment, such as pipelines, valves, flowmeters, pumps and the like.

In the case of a fixed bed reactor, the feed streams can be fed at the bottom of the reactor, preferably below the fixed catalyst bed, in an upflow-mode or the reactants can be fed at the top of the fixed bed reactor, preferably above the fixed bed in a down-flow or trickle bed procedure.

In a fixed bed reactor, the catalyst is usually arranged in a fixed bed. If the catalyst is arranged as a fixed bed, it is preferred to shape the catalyst into suitable shapes, such as tables, cylinders or other extrudates. The catalyst bed optionally contains inert particles which are, for instance, interspersed throughout the bed and/or form discrete layers, e.g., at an end or intermediary to the bed. Preferably, flow through a catalyst bed is substantially plug flow. The proportion of the packing elements in such catalyst preparations can be from 20 to 80 parts by volume, preferably from 30 to 60 parts by volume and particularly preferably from 40 to 50 parts by volume.

In batch reactors, it is advantageous to add catalysts in form of a slurry, such as a powder or other shaped particles, such as tablets, cylinders or other extrudates.

The conversion of glycolaldehyde with the aminating agent is typically performed at a pressure of 1 to 500 bar, preferably 10 to 350 bar, more preferably at a pressure of 50 to 300 bar and most preferably 80 to 220 bar. The pressure is maintained or controlled generally via the metered addition of the hydrogen.

The conversion of glycolaldehyde with aminating agent generally proceeds at temperatures of 15 to 350° C., preferably 50 to 250° C., more preferably 80 to 220° C.

The residence time in the GA-reactor according to the invention, in the case of performance in a batchwise process, is generally 15 minutes to 72 hours, preferably 60 minutes to 24 hours, more preferably 2 hours to 10 hours.

In the case of performance in a preferred continuous process, the catalyst hourly space velocity is generally in the range from 0.01 kg of glycolaldehyde/kg of catalyst/h to 3.0 kg of glycolaldehyde/kg of catalyst/h, preferably 0.05 kg of glycolaldehyde/kg of catalyst/h to 2.0 kg of glycolaldehyde/kg of catalyst/h and more preferably 0.1 kg of glycolaldehyde/kg of catalyst/h-1.5 kg of glycolaldehyde/kg of catalyst/h.

The product stream obtained from the conversion of glycolaldehyde with the aminating in the process according to the invention may comprise unreacted glycolaldehyde and unreacted aminating agent.

Additionally, the product stream comprises substituted and unsubstituted ethyleneamines, ethanolamines and aminoethylamines.

If the aminating agent is ammonia, the product stream preferably comprises ethylenediamine, monoethanolamine, diethanolamine and triethanolamine.

If the aminating agent is a primary alkylamine, the product stream preferably comprises N-alkylethanolamine, N-alkyl-diethanolamine and dialkylethylenediamine. Accordingly, when methylamine (MA) is used as an aminating agent, the product stream comprises N-methyl-ethanolamine, N-methyl-diethanolamine and dimethyldiethylenediamine.

If the aminating agent is a secondary alkylamine, the product stream preferably comprises dialkylethanolamine and tetralkylethylenediamine. Accordingly, when dimethylamine (DMA) is used as an aminating agent, the product stream comprises dimethylethanolamine (DMEOA) and tetramethylethylenediamine (TMEDA).

In addition, the product stream comprises one or more organic carboxylic acids.

Further, the product stream may comprise one or more solvents.

In addition, the product stream may comprise other components, which were fed to the GA-reactor or which were formed as side-products during the conversion reaction, such as oxygenates, e.g. formaldehyde, hydroxyacetone (acetol), glyoxal, dihydroxyacetone, methylglyoxal (pyruvaldehyde), methanol and acetone.

The product stream is preferably refined by performing at least one of the following work-up steps:
  (i) Contacting the product stream with a base;
  (ii) Contacting the product stream with an anion exchanger;
  (iii) Distillation.

In a preferred embodiment, the product stream is contacted with a base.

Preferred bases form a high boiling salt with the one or more acids present during the conversion of glycolaldehyde with the aminating agent.

Preference is given to hydroxides of alkaline metals, in particular LiOH, NaOH and KOH, hydroxides of alkaline earth metals, in particular Ca-hydroxide;

alkali methoxides, in particular NaOMe, KOMe; and basic metal oxides or basic metal carbonates, in particular CaO, $CaCO_3$, MgO, $Na_2$ and $K_2O$.

The base is usually added in quantities sufficient to neutralize the acids present during the conversion of glycolaldehyde. Neutralization is usually affected prior to distillation. If the salt precipitated from the product mixture, the precipitates may be removed by conventional solid-liquid separation techniques, such as filtration.

More preferably, the salts remain in the sump during distillation and are preferably discharged as waste products together with other high boiling side-products.

In a further preferred embodiment, the product stream is contacted with an anion exchanger.

Anion exchangers may comprise strongly basic functional groups, such quaternary ammonium groups, e.g. trimethylammonium groups.

The anion exchangers may also comprise weak basic functional groups, such as primary, secondary or tertiary amino groups.

In the regenerated state, basic anion exchangers comprise hydroxide anions as counterions to the basic groups of the anion exchanger.

When contacting the product stream with the anion exchanger, the hydroxide anions are exchanged against the carboxylate anions of the acids present during the conversion of glycolaldehyde with the aminating agent. When the anion exchanger is fully loaded, the anion exchanger is preferably regenerated by passing a strong base, such as NaOH or KOH over the anion exchanger and thereby flushing out the absorbed carboxylate anions.

In a preferred embodiment, the product stream is subjected to distillation. The distillation may be conducted as a sequence of distillation steps using conventional distillation columns or divided wall columns. For example, the destillative work-up of ethyleneamines and ethanolamines is well-established in the state of the art and can be found in further detail in the Process Economic Program Report No. 138 "Alkyl Amines" published by SRI International, Menlo Park, California, March 1981, and comprises the steps of hydrogen removal, removal of the aminating agents, such as ammonia, DMA or MA, and separation of the obtained products and side products.

The advantages of the present invention are that it has been possible to develop a process for converting glycolaldehyde which enables a high conversion of glycolaldehyde and an increased selectivity for conversion products of glycolaldehyde in which the terminal hydroxyl group of glycolaldehyde is converted. Further, when converting glycolaldehyde with DMA, the conversion shows an increased selectivity for TMEDA.

EXAMPLES

The process according to the invention is illustrated in detail with reference to the examples adduced below.

Example 1 (Reference Example)

25 mmol of glycolaldehyde dimer (corresponds to 50 mmol of monomeric glycolaldehyde), 141 mmol of dimethylamine, 60 g of THF and 3 g of a nickel catalyst were transferred to an autoclave under a nitrogen atmosphere.

The nickel catalyst used in the reaction was a powder of nickel supported on silica, commercially available as Ni-5249P.

At room temperature, the pressure was increased to 10 bar by injecting hydrogen into the autoclave.

Then, the autoclave was heated to 130° C.

Upon reaching 130° C., the pressure was increased to 175 bar by injecting further hydrogen into the autoclave.

Upon reaching 175 bar, the reaction mixture was stirred for one hour.

Thereafter, the reaction mixture was cooled to room temperature and the autoclave was depressurized and flushed with nitrogen gas.

The reaction mixture was analyzed by gas chromatography.

The composition of the reaction mixture (without solvents) is given in area percent and was as follows:
TMEDA: 55%
DMEOA: 26%
MEG: 1%

Example 2 (Reference Example)

Example 2 was identical to Example 1, with the exception, that the nickel catalyst used in Example 1 was reused in Example 2 and maintaining the catalyst under inert conditions (nitrogen atmosphere) when charging and discharging the autoclave. In this way, the glycolaldehyde in Example 2 is contacted with an activated catalyst, because activation of the catalyst occurred in-situ in Example 1.

The composition of the reaction mixture (without solvents) is given in area percent and was as follows:
TMEDA: 26%
DMEOA: 76%
MEG: 2%

Example 3: Conversion in the Presence of Organic Carboxylic Acid

Example 3 was identical to Example 1, with the exception that a carboxylic organic acid in an amount indicated in Table 1 was charged to the autoclave together with the other reactants.

The composition of the reaction mixture (without solvents) is given in area percent and is also depicted in Table 1.

After discharging the reaction mixture obtained during a first run under inert conditions, the reaction was repeated (second run) by charging the reactor with the same amount of components as in the first run and carrying out the reaction in the same way the reaction was carried out in the first run. The only difference between the first run and the second run was that the catalyst used in the second run is an activated catalyst which was activated in situ during the first run.

TABLE 1

| Organic carboxylic acid | Run No. | Amount of acid | Solvent | TMEDA | DMEOA | MEG |
|---|---|---|---|---|---|---|
| None (Example 1) | 1 | — | THF | 55 | 32 | 1 |
|  | 2 |  |  | 26 | 76 | 2 |
| Lactic acid | 1 | 1 mmol | THF | 56 | 34 | 1 |
|  | 2 |  |  | 67 | 22 | 0 |
| Lactic acid | 1 | 10 mmol | THF | 66 | 20 | 0 |
|  | 2 |  |  | 63 | 23 | 0 |
| Acetic acid | 1 | 10 mmol | THF | 69 | 5 | 0 |
|  | 2 |  |  | 59 | 5 | 0 |
| Glycolic acid | 1 | 10 mmol | THF | 73 | 11 | 0 |
|  | 2 |  |  | 39 | 4 | 0 |
| Lactic acid | 1 | 10 mmol | THF/water | 18 | 22 | 3 |
|  | 2 | 10 mmol |  | 65 | 14 | 1 |
| Formic acid | 1 | 10 mmol | THF | 60 | 12 | 0 |
| Formic acid | 2 | 10 mmol |  | 65 | 7 | 0 |

Without the addition of organic carboxylic acids, the selectivity of the reaction drastically changes from TMEDA to DMEOA when the catalyst is reused. The catalyst is activated during the first run. Therefore, after the first run, the selectivity will shift from TMEDA to DMEOA.

Such a shift in selectivity can be prevented when adding an organic carboxylic acid according to the invention. Accordingly, it can be shown that the organic carboxylic acid acts as selectivity modifier and maintains a strong selectivity for conversion products of glycolaldehyde in which the terminal hydroxyl group of glycolaldehyde is converted.

Example 4: Conversion Over Cu-Catalyst in the Presence and Absence of an Organic Acid 8.3 mmol of glycolaldehyde dimer (16.6 mmol of monomeric glycolaldehyde), 50 mL of a 2.0 molar solution of DMA in THF (100 mmol) were put into a 160 mL steel autoclave and 5 g of a reduced copper catalyst (containing 68% Cu-oxide prior to reduction) soaked in THF was placed in a steel mesh basket that was fixed to the head of the autoclave. The autoclave was closed, flushed with argon, and a hydrogen pressure of 20 bar was applied. Then it was heated under stirring (mechanical stirrer with pitched blades) to 130° C. and the pressure was adjusted to 125 bar with hydrogen. Upon reaching this pressure the reaction mixture was stirred for 2 hours. Thereafter, the reaction mixture was cooled to room temperature and the autoclave was depressurized. The reaction mixture was analyzed by gas chromatography.

In two further experiments, 0.1 mL formic and 0.1 mL lactic acid were added to the mixture of DMA and glycolaldehyde dimer in THF. All results are listed in Table 2. The composition of the reaction mixture (calculated without solvents and DMA) is given in area-%:

TABLE 2

| Organic carboxylic acid | Amount of acid | Solvent | TMEDA | DMEOA |
|---|---|---|---|---|
| None | — | THF | 71 | 23 |
| Formic acid | 2.6 mmol | | 75 | 4 |
| Lactic acid | 1.3 mmol | THF | 86 | 4 |

The invention claimed is:

1. A process for the conversion of glycolaldehyde with an aminating agent in the presence of hydrogen and of a catalyst in a glycolaldehyde conversion reactor, wherein one or more organic carboxylic acids are fed into the glycolaldehyde conversion reactor.

2. The process according to claim 1, wherein the one or more organic carboxylic organic acids are selected from the group consisting of
saturated aliphatic monocarboxylic acids,
unsaturated aliphatic monocarboxylic acids,
saturated aliphatic dicarboxylic acids
unsaturated aliphatic dicarboxylic acids,
aryl carboxylic acids, and
hydroxy carboxylic acids.

3. The process according to claim 1, wherein the one or more organic carboxylic acids are selected from the group consisting of formic acid, acetic acid, propionic acid, acrylic acid, levulic acid, lactic acid, glycolic acid and pyruvic acid.

4. The process according to claim 1, wherein the molar ratio of glycolaldehyde to each selected organic carboxylic acid fed into the glycol conversion reactor is in the range of 1:1 to 100:1.

5. The process according to claim 1, wherein the molar ratio of glycolaldehyde to the total amount of organic carboxylic acids fed into the glycol conversion reactor is in the range of 1:1 to 300:1.

6. The process according to claim 1, wherein one or more solvents are fed into the glycolaldehyde conversion reactor.

7. The process according to claim 1, wherein one or more solvents are selected from the group consisting of methanol, tetrahydrofuran and water.

8. The process according to claim 1, wherein the glycolaldehyde, the aminating agent, the organic carboxylic acid and optionally one or more solvents are fed separately to the glycolaldehyde conversion reactor or wherein at least two of the aforementioned components are mixed to obtain mixed feed streams comprising two or more components.

9. Process according to claim 1, wherein the mixed feed stream comprises 5 to 50 percent by weight of glycolaldehyde, 0.1 to 25 percent by weight of organic carboxylic acids, 0.1 to 25 percent by weight of other organic components, rest water.

10. The process according to claim 1, wherein the mixed feed stream is obtained by the hydrous thermolysis of sugars or from the pyrolysis of wood.

11. The process according to claim 1, wherein the aminating agent is a compound of formula (I)

in which
R$^1$, R$^2$ are hydrogen (H), alkyl such as C$_{1-20}$-alkyl, cycloalkyl such as C$_{3-12}$-cycloalkyl, alkoxyalkyl such as C$_{2-30}$-alkoxyalkyl, dialkylaminoalkyl such as C$_{3-30}$-dialkylaminoalkyl, aryl, aralkyl such as C$_{7-20}$-aralkyl, and alkylaryl such as C$_{7-20}$-alkylaryl, or together are —(CH$_2$)$_j$—X—(CH$_2$)$_k$—,
X is CH$_2$, CHR$^3$, oxygen (O), sulfur(S) or NR$^3$,
R$^3$ is hydrogen (H), alkyl such as C$_{1-4}$-alkyl, alkylphenyl such as C$_{7-40}$-alkylphenyl,
j, k are each integers from 1 to 4.

12. The process according to claim 1, wherein the aminating agent of formula (I) is (i) an alkylamine in which R$^1$ is H and R$^2$ is C$_{1-20}$-alkyl or (ii) a dialkylamine in which R$^1$ and R$^2$ are each—the same or different—C$_{1-20}$-alkyl.

13. The process according to claim 1, wherein the molar ratio of glycolaldehyde to aminating agents is in the range of 1:100 to 100:1.

14. The process according to claim 1, wherein the catalyst comprises one or more metals selected from groups 7, 8, 9, 10 and 11 of the periodic table of elements.

15. The process according to claim 1, in wherein the effluent from the glycolaldehyde conversion reactor is refined by performing at least one of the following steps:
(i) Contacting the effluent with a base;
(ii) Contacting the effluent with an anion exchanger;
(iii) Distillation.

* * * * *